United States Patent
Wei et al.

(10) Patent No.: US 6,541,046 B2
(45) Date of Patent: Apr. 1, 2003

(54) HERBAL COMPOSITION AND METHOD FOR CONTROLLING BODY WEIGHT AND COMPOSITION

(76) Inventors: Kaiyuan Wei, deceased, late of Beijing (CN); by Xiurong Xu, legal representative, Building Li Ze San Lou, Apt. 6-401, Dormitory of Beijing Normal University, Beijing (CN), 100875; by Wei Jing, legal representative, Building Li Ze San Lou, Apt. 6-401, Dormitory of Beijing Normal University, Beijing (CN), 100875; by Wei Xian, legal representative, 1$^{st}$ Xinglong Street, Xidan, Beijing (CN), 100031; by Wei Hong, legal representative, 20-2-12 Weigongcun Zone, Haidian District, Beijing (CN), 100081

( * ) Notice: Subject to any disclaimer, the term of this patent is extended or adjusted under 35 U.S.C. 154(b) by 0 days.

(21) Appl. No.: 10/054,694

(22) Filed: Jan. 17, 2002

(65) Prior Publication Data

US 2002/0164387 A1 Nov. 7, 2002

(30) Foreign Application Priority Data

Feb. 12, 2001 (CN) .......................................... 01103777 A (51) Int. Cl.$^7$ ....................... A61K 35/78; A61K 39/385

(52) U.S. Cl. ...................... 424/756; 424/773; 424/746; 424/725

(58) Field of Search ............................... 424/725, 195.1, 424/746, 756, 773

(56) References Cited

U.S. PATENT DOCUMENTS 6,264,995 B1 * 7/2001 Newmark et al. .......... 424/725

FOREIGN PATENT DOCUMENTS

| CN | 10881367 | * | 2/1994 |
| CN | 1257709 A | * | 6/2000 |

* cited by examiner

Primary Examiner—Leon B. Lankford, Jr.
Assistant Examiner—Patricia Patten
(74) Attorney, Agent, or Firm—Orrick, Herrington & Sutcliffe LLP; Kurt T. Mulville (57) ABSTRACT

The present invention relates to a dietary supplement for the treatment of obesity, including both weight loss and reduction of weight gain. Pursuant to the invention, a decoction of a herbal mixture, comprising rhubarb, red saga root, astragalus, turmeric, and dried ginger and various combinations thereof, provides therapeutic weight loss as well as lipid reduction and change body composition. The invention includes methods of manufacture and administration and also includes the herbal decoction in various forms of administration and in combination with food.

6 Claims, 4 Drawing Sheets

HERBAL COMPOSITION AND METHOD FOR CONTROLLING BODY WEIGHT AND COMPOSITION

RELATED INFORMATION

This application claims priority to Chinese Patent Application No. 01103777.6 filed Feb. 12, 2001, entitled "COMPOSITION AND METHOD FOR EFFECTING WEIGHT REDUCTION" and the disclosure is hereby incorporated by reference.

FIELD OF THE INVENTION

The present invention generally relates to dietary supplements and foods for reducing weight gain, effecting weight loss and causing favorable changes in body composition. More specifically, the invention relates to the field of herbal compositions, especially decoctions for oral administration containing rhubarb and other herbal ingredients.

BACKGROUND OF THE INVENTION

Body weight and body composition is determined by the competing balance of food intake and energy expenditure. Although both genetic and environmental factors can contribute to obesity, the most common cause of weight gain and an overweight body composition is excessively high caloric intake accompanied by a lack of physical activity. The resulting accumulation of surplus fat places overweight or obese individuals at increased risk of illness from hypertension, lipid disorders, type 2 diabetes, coronary heart disease, stroke, gallbladder disease, osteoarthritis, sleep apnea and respiratory problems, certain cancers, and a wide variety of other diseases and undesired physiological conditions, as well as overall mortality. According to a study, the proportion of overweight individuals in the United States increased from 25% in 1980 to 33% in 1991. (Third National Health and Nutrition Examination Survey, 1991). In 1998 the National Institutes of Health reported that over 55 percent of the U.S. population are now considered overweight or obese. (*Obesity Clinical Guidelines: NIH Statement Jun.* 3, 1998, press release).

Obesity may become partially reversed or prevented by employing diet or nutrition and behavior modification programs or by using pharmaceutical intervention. Among the most widely administered drugs are: orlistat, which reduces the amount of dietary fat that is absorbed from the intestine; sibutramine, which suppresses appetite by inhibiting the re-uptake of norepinephrine and serotonin; fenfluramine and d-fenfluramine, which suppress appetite by both releasing serotonin and then inhibiting its re-uptake; and phentermine, which suppresses the appetite by stimulating the release of norepinephrine.

Most weight reduction drugs typically achieve only a 5–10% decrease in body weight. (*National Task Force on the Prevention and Treatment of Obesity: Long-term pharmacotherapy in the Management of Obesity*, JAMA 276:1907–15, 1996). In addition, most drugs have mild to serious side effects. For example, the once popular appetite suppressant drug "Fen-Phen" (the combination of fenfluramine and phentermine), which gave a 15–20% reduction in body weight, was clinically determined to have significantly increased the risk of heart valve damage. (F. Brenot et al., Appetite Suppressant Drugs and the Risk of Primary Pulmonary Hypertension, N. Engl. J. Med., 335:609–16, 1996). Consequently, after a number of confirmed "Fen-Phen"—related patient deaths, most of the drugs containing fenfluramine have been recalled and withdrawn. (Connolly H. M. et. al., N. Eng. J. Med. 337:581–88, 1997). In 1999 the FDA removed fenfluramine from the market. Other common side effects include dizziness, headaches, rapid pulse, palpitations, sleeplessness, hypertension, diarrhea, and intestinal cramping.

In addition to adverse side effects, current weight loss drugs may be habit forming, as exemplified by drugs containing amphetamines, and the initial weight reducing effect of many drugs wears off over time, requiring increased dosages to maintain weight reduction. The most serious problem, however, is that the lost weight is frequently regained after the drug is discontinued and the fairly limited utility of these drugs is more than offset by the side effects and other drawbacks inherent in their use.

The following table provides a synopsis of some of the characteristics of the most popular weight loss drugs and notes some of the impediments to wide-scale use:

| Generic Name and Mechanism | Brand Name | Comments |
|---|---|---|
| Amphetamine + Dextroamphetamine sympathomimetic amine appetite suppressants | Adderall | Not commonly used therapeutically for obesity. High abuse potential. |
| Benzphetamine sympathomimetic amine appetite suppressant | Didrex; Benzfetamine | Not commonly used therapeutically. High abuse potential. |
| Bromocriptine stimulates dopamine type-2 receptors and antagonizes type-1 receptors in brain | Ergoset; Parlodel | Not approved in US for obesity. Used "off label". |
| Dexfenfluramine appetite suppressant via serotonin release and serotonin reuptake block; the d isomer of fenfluramine; thought to be less addicting than most others | Redux | Approved 04/96 in US with no limit on duration of use. Voluntarily withdrawn in US 09/15/97 due to heart valve damage. |
| Dextroamphetamine sympathomimetic amine appetite suppressant | Dexedrine | Not approved in US for obesity. Used "off label". Highly abused. |
| Diethylpropion sympathomimetic amine appetite suppressant | Amfepramone; Tenuate; Tenuate Dospan | Possible link to primary pulmonary hypertension |
| Fenfluramine racemic mixture dexfenfluramine and L-fenfluramine; mechanism like dexfenfluramine (see above), except also affects dopamine availability | Pondimin; Ponderal | One component of "fen/phen"; Approved in US in 1973. Voluntarily withdrawn in US due to heart valve damage 09/15/97 |
| Fluoxetine selective serotonin reuptake inhibitor (SSRI) | Prozac | Not approved in US for obesity. FDA application was withdrawn by manufacturer. Used "off label". |
| Mazindol sympathomimetic amine appetite suppressant | Mazanor; Sanorex | Approved in US in 1973. Rarely used. High abuse potential. |
| Methamphetamine sympathomimetic amine appetite suppressant | Desoxyn; Methampex | Rarely used for obesity. High abuse potential. |
| Orlistat not a CNS-active drug; decreases the amount of fat absorbed from the diet by 30%. | Xenical | Recommended for approval in US 05/15/97; FDA panel reconsidered and split 5-5 on 03/16/98; due to possible link to breast cancer |
| Phendimetrazine sympathomimetic amine appetite suppressant | Adipost; Anorex; Bontril; Parzine; | Approved in US in 1961. Rarely used. |

-continued

| Generic Name and Mechanism | Brand Name | Comments |
|---|---|---|
| Phentermine sympathomimetic amine appetite suppressant | Phendiet; Plegine; Wehless Adipex-P; Fastin; Ionamin; Oby-Cap; Phentamine; T-Diet; Zantryl | Approved as "resin complex" in 1959. Approved as hydrochloride in 1973. The other component of "fen/phen". |
| Phenylpropanolamine sympathomimetic amine appetite suppressant | Acutrim; Dexatrim; Phenoxine; Phenyldrine; Propagest; Rhindecon | Available "over the counter". |
| Sibutramine inhibits reuptake of dopamine, norepinephrine, and serotonin in brain | Meridia | Approved in US, 11/97 |

Various natural herbal weight reduction formulas have been suggested as safer alternatives to both prescription and over-the-counter weight loss compounds. Generally, herbal weight loss formulas have fewer side effects when properly formulated and administered. Despite the fact that herbs are natural substances, however, some herbal formulas can still be abused. For example, improper administration of herbal weight loss formulas based primarily on ma huang (ephedra) and high caffeine-containing herbs, such as guanrana and kola nut, may result in diminished energy and a depleted body.

New compounds for treatment of humans are often tested in animal models to insure their safety and efficacy. A number of rat models have been used to study the effect of drugs on obesity. Diet-related obesity can be created in the Osbom-Mendel, Wistar and Sprague-Dawley rats by altering their diets to increase caloric consumption. This is usually accomplished by increasing the percentage of fat in a carefully controlled diet and measuring a series of physiologic parameters that indicate changes in energy metabolism, weight gain, weight loss, body composition, and other indicia of overall health and the balance between food intake and energy expenditure. These rats experience the increased weight and fat deposition characteristically seen in obese humans. Using these models, compounds that are candidates for agents to control body weight and composition are tested for safety and efficacy. Typically, drugs that prevent weight gain or cause weight loss in rat models are also effective in humans, albeit at a slightly lower level of efficacy. Given the serious problems associated with obesity, and the significant drawbacks associates with many weight loss compounds, a need exists for a safe and effective composition that reduces weight gain, causes weight loss, and improves body composition.

SUMMARY OF THE INVENTION

The present invention is comprised of compositions and methods for effecting weight reduction, specifically, herbal formulations and methods for their administration to reduce body weight prevent weight gain and lower blood lipid and sugar levels. At the physiological level, the compositions alter the balance of food intake and energy metabolism to favor weight reduction and the improvement of body composition by reduction of fat and overall lipid levels. The compositions are comprised of a combination of more than one herb, and specifically chemical extracts from herbs, that are formulated in a special combination such that the individual components are combined for their individual utilities in the weight loss context, as well as for their synergistic effect in the complete composition of the invention. Each herb is identified by its botanical characteristics, as well as by the chemical compounds contained within the plant that may be extracted by chemical manufacturing processes. Accordingly, chemical compounds and individual constituents of the herbs, individually and collectively, that mimic the effect of the herbs and herbal extracts may be substituted for the actual herbs obtained from nature without departing from the spirit and utility of the invention. In a preferred embodiment, the compositions of the invention include another rhubarb that is specially processed in a decoction and used in combination with other herbal compositions and extracts that enhance the physiological utility of rhubarb and its derivatives. In a preferred embodiment, the composition contains the functional chemical components of rhubarb in combination with other agents that allow the ingestion of rhubarb extracts without side effects.

In use, the compositions of the invention can be administered orally in a liquid or tablet form and may be combined with food as part of an obesity treatment regimen or as a dietary or fitness supplement. When provided to non-humans, the compositions of the invention may be administered separately or may be combined with ordinary feed or liquid nourishment to effect the alterations in body composition as described herein. Thus, the compositions of the invention include the herbal compositions described herein in oral dosage form, or in combination with any of the usual pharmaceutical or nutritional media employed in the art for oral liquid preparations, e.g., suspensions, elixirs, and solutions. Generally, media containing water, oils, alcohols, flavoring agents, preservatives, coloring agents and the like may also be used for flavor, texture, or shelf-life enhancement. Carriers such as starches, sugars, diluents, granulating agents, lubricants, binders, disintegrating agents, and the like may be used to prepare oral solids (e.g., powders, capsules, pills, and tablets). Controlled release forms may also be used. Because of their ease in administration, tablets, pills, and capsules represent advantageous oral dosage unit forms, in which case solid pharmaceutical carriers are employed. If desired, tablets may be sugar coated or enteric coated by standard techniques. While the herbs and herb extracts of the invention are naturally derived from plants that are edible, the compositions of the invention can be administered as herbs or direct extracts of herbs, but one or more herbs can also be substituted with the chemical compounds or functional equivalents that are derived from such herbs. For example, one component of an embodiment of the invention is turmeric. The main functional ingredient of turmeric is known to be curcumin, an organic molecule whose structure and function are well known. Thus, consistent with the invention, the turmeric herb may be replaced in some applications with the organic molecule contained therein. Moreover, the compositions of the invention can be combined with ordinary foods to enhance the value of the weight control capabilities. For example, the compositions can be mixed with soft drinks, food supplements, candy, or high-energy bars, and virtually any other food that can be supplemented with a powder or liquid. Thus, the invention specifically includes food substances of specific types combined with the composition of the invention in specified forms and quantities.

A preferred embodiment of the herbal formulation is comprised of a combination of rhubarb root and stem (*radix*

*et rhizoma rhei*), astragalus root (*radix astragali*), red sage root (*radix salviae miltiorrhizae*), turmeric (*rhizoma curcumae longae*), and dried ginger (*rhizoma zingiberis officinalis*). The herbal formulations are preferably administered orally in a dosage range that results in a decrease of body weight, normalization of the metabolic rate, and reduction of blood lipid and sugar level. In a preferred experimental application of the invention, rats administered with 5 grams per day of the herbal composition lost about 39% of their pretreated weight and 60% of their pretreated cholesterol level.

DETAILED DESCRIPTION OF THE INVENTION

The present invention is a pharmaceutically acceptable herbal composition, usually administered as a dietary supplement, to effect weight loss, a reduction in weight gain, or an alteration in body composition. For the purposes of this invention, "pharmaceutically acceptable" compositions are formulated and administered to be non-toxic and, when desired, used with carriers or additives that are approved for administration to humans and animal species. In a preferred embodiment, the composition comprises a decoction of rhubarb root and stem, (*radix et rhizoma rhei*), in combination with other compounds or compositions to enhance the tolerance of rhubarb and increase the efficacy and safety of a formulation derived from a rhubarb-containing decoction. These include astragalus root (*radix astragali*), red sage root (*radix salviae miltiorrhizae*), turmeric (*rhizoma curcumae longae*), and dried ginger (*rhizoma zingiberis officinalis*). When the composition of the invention is added to solid food stuffs, the composition is preferably prepared in a powder form that is constituted from the decoction by conventional techniques. Preferably, depending on the composition and mode of administration, the dosage is between 2 grams to approximately 90 grams and is orally administered on a daily basis. Most preferably, however, approximately 22.5 grams is taken orally each day. For ease of reference, the several different formulations of the invention are collectively referred to herein as the "DRD" decoction.

Rhubarb (*radix et rhizoma rhei*), also known as "da huang" in traditional Chinese medicine, is an anti-inflammatory and diuretic herb whose effectiveness is controlled by the amount used. In the preferred embodiment of the invention, species of the genus Rheum are used, species of the botanical name Rheum tanguticum Maxim ex Balf, and 2 species of Chinese Rhubarb of the botanical name Rheum palmatum L, and Rheum officinale Baill. From the foregoing, Rheum tanguticum Maxim ex Balf is particularly preferred. When taken in small doses, rhubarb functions as a digestive aid, increases salivary and gastric flow, improves appetite, and cleanses the liver by encouraging bile flow. This cleansing action also encourages the healing process of duodenal ulcers and enhances gallbladder function. Rhubarb has also been described as containing anthraquinones, specifically rhein, emodin, aloe emodin, chrysophanol, and physcion. These compounds are known to exhibit antibiotic functions, and the anthraquinone glycosides (rhein-8-monoglucoside, emodin-6-monoglucoside, aloe emodin-8-monoglucoside, chrysophanol-1-monoglucoside, physcionmonoglucoside are known to exhibit diarrheal function. (Chirikdjian J J, et al. Planta Medica, 1983, (48(1): 34). Also, rhein and emodin inhibit tumor growth in mice.

In large doses, rhubarb can be used for emptying the bowels thoroughly. As a gentle laxative, rhubarb strengthens the gastrointestinal tract, and tones and tightens bodily tissues. Although known for its therapeutic properties in treating dysenteric conditions, rhubarb also has a beneficial effect on blood chemistry, enhances blood circulation, and lowers serum cholesterol.

Only roots and root stems of the rhubarb plant are used for medicinal purposes because the leaves are potentially toxic. In addition, rhubarb plants from different climatic regions possess different properties. Preferably, the rhubarb roots used in the preferred embodiments of the present invention are those found Longxi in the Garson Province and other areas in North Central China.

As an essential ingredient of the present invention, the rhubarb root plays key roles in reducing fat intake, enhancing metabolism and decreasing blood lipid or sugar level. The relative weight percentage of the rhubarb in the preferred embodiments of the decoction is between about 36% to about 44%. In one preferred embodiment of the present invention, the composition contains 40% of the rhubarb roots.

Turmeric (*rhizoma curcumae longae*) promotes blood circulation. In the natural form, curcumin has been described as containing the following compounds: curcumin and turmerone. The most well-characterized component of turmeric is curcumin. Curcumin has the structure shown in (I)

(I)

where $R_1$ is —$OCH_3$; $R_2$ is —OH; $R_3$ is —H; $R_4$ is —H; $R_5$ is —$OCH_3$; $R_6$ is —OH, and $R_7$ is H. Curcumin has the chemical name (E, E) 1,7-bis(4-hydroxy-3- methoxyphenyl)-1,6-heptadiene-3,5-dione. In natural curcumin, the carbon-carbon double bonds are in the trans configuration.

Curcumin is known to inhibit the enzymatic transformation between phosphorylase b and phosphorylase a. (*Curcuma longa;* S. Reddy S & B. B. Aggarwal, "Curcumin is a Non-Competitive and Selective Inhibitor of Phosphorylase Kinase," *FEBS Lett.* 341:19–22 (1994)). The antiproliferative properties of curcumin inhibit tumor initiation induced by benzo[a]pyrene and 7,12 dimethylbenz[a] anthracene (M. T. Huang et al., *Carcinozenesis* 13:2183–2186 (1992); M. A. Azuine & S. V. Bhide, *Nutr. Cancer* 17:77–83: (1992). Curcumin inhibits the tumor promotion caused by phorbol esters (M. T. Huang et al., *Cancer Res.* 48:5941–5946 (1998); A. H. Conney et al., *Adv. Enzyme Regul.* 31:385–396 (1991); Y. P. Lu et al., "Effect of Curcuminon 12-O-Tetradecanoylphorbol-13-Acetate and Ultraviolet B Light-Induced Expression of c-Jun and c-Fos in JB6 cells and in Mouse Epidermis," *Carcinogenesis* 15:2263–2270 (1994) and has been shown to inhibit pp60src (epidermal growth factor equivalent) tyrosine kinase via inhibition of phosphorylase kinase.

Curcumin is an inhibitor of Type I cyclic AMP-dependent protein kinase, the enzyme mainly responsible for activating phosphorylase kinase. The inhibition is competitive with respect to both ATP and the substrate (M. Hasmeda & G. M. Polya, "Inhibition of CyclicAMP-Dependent Protein Kinase by Curcumin," *Phytochemistry* 42:599–605 (1996)). Phosphorylase kinase, in turn, increases the migration of inflammatory cells, tumor cells, smooth muscle cells, and other cell types, as discussed above, as well as infectious organisms, increasing both the destructive and proliferative sequelae of the inflammatory response.

Accordingly, an improved method of treatment of wounds, burns, acne, and eczema, as well as skin damage resulting from exposure to sunlight or exposure to cigarette smoke or nicotine, utilizes inhibition of phosphorylase kinase activity in the affected skin in a mammal, particularly a human. A particularly suitable reagent for inhibiting phosphorylase kinase activity is curcumin.

Turmeric is also often used to treat conditions such as amenorrhea, dysmenorrhea and other pains in the abdominal region caused by stagnation of blood. In addition, turmeric has antibiotic and anti-inflammatory properties that make it an herbal medicine for a wide variety of other conditions ranging from arthritis to ulcers, flatulence, blood in the urine, bruises, colic, respiratory diseases, chest pains, jaundice, hepatitis, diabetes, menstrual irregularities, hemorrhage, and toothache. It is also effective both as a treatment and a preventive for intestinal parasites.

Even in high doses, turmeric has not been shown to have any toxicity. Curcumin, the compound responsible for turmeric's yellow color, is considered its primary anti-inflammatory component. See Ammon et al., U.S. Pat. No. 5,401,777, Heng U.S. Pat. No. 5,925,376. Dimethylbenzyl alcohol, another component of turmeric, benefits the cardiovascular system by normalizing cholesterol, first by reducing it in the blood and then by removing its accumulation in the liver. Turmeric is known for removing arterial plaque, effectively treating anemia, and as a potent hemostatic used to reduce bleeding.

Turmeric's antioxidant properties are often regarded as more potent than either vitamin C or E. Turmeric's antioxidant properties also account for its use as a food preservative and an inhibitor of rancidity of fats and oils. Turmeric also promotes digestion and can increase bile output by up to 100%.

In addition to the rhubarb roots described above, turmeric is another ingredient of the invention that enhances metabolism and reduces blood lipid and sugar level. The relative weight percentage of the turmeric in the preferred embodiment of the decoction is between about 24% and about 30% of the herbal composition. In one preferred embodiment of the invention, the composition contains 26–27% turmeric.

Astragalus root (*radix astragali*) enhances the immune system and helps the body resist virus infections, particularly in the lungs, by increasing production of interferon, an immune factor that inhibits viral growth. Astragalus polysaccharides are known to enhance immune function. The compounds stragaloside I, astragaloside II, astragaloside III, and astragaloside IV are anti-oxidants, and especially inhibit lipid oxidation (CA 1987, 107: P195156p). In the natural form, astragalus has been described as containing astragalan, astragaloside I, astragaloside II, astragaloside III, and astragaloside IV, and astragolin. It also helps eliminate toxins and promote the healing of damaged tissues, including protecting the liver against chemical damage. In the preferred embodiment, Astragalus or "milk retch root" from the Bantou region of Inner Mongolia is preferred. This species has the botanical name Astragalus membranaceus Bge. Var. mongholicus.

In addition, astragalus increases the production and activity of white blood cells (i.e., T-cells) specifically involved in fighting disease. Clinical studies have shown that cancer patients who take astragalus while undergoing chemotherapy, which severely inhibits natural immune responses, recover faster and live significantly longer than those that do not use this herb. Astragalus eases chemotherapy and radiation side effects and inhibits the spread of tumors.

Astragalus is rich in polysaccharides and contains glycosides, saponins, and essential fatty acids. Moreover, astragalus helps prevent clotting and has systemic vasodiation properties that help prevent coronary heart disease and improve blood circulation. Its heart tonic properties also lower blood pressure, dilate blood vessels, and strengthen the heart. Furthermore, astragalus facilitates digestion and alleviates digestive ailments. It increases the flow of bile and digestive fluids and, thus, increases metabolism and helps control diarrhea.

The astragalus plant grows to a height of about 1 meter, with rigid stalks that sprout eight to twelve pairs of leaflets. The medicinal root is covered with a tough, fibrous, yellowish brown skin and is typically sold in flexible slices approximately 15–20 centimeters long. The marrow is yellowish white and has a sweet taste that resembles licorice. The herb is grown mostly in northern China, Japan, and Korea, each region producing its own distinctive variety. All types can be used in formulas calling for astragalus; as noted above, preferred medicinally potent varieties come from inner Mongolia and northern China.

Astragalus also enhances the overall body energy level, thereby helping to compensate for any possible depleted energy which is often caused by weight loss. In the context of the preferred embodiments of the present invention, astragalus works together with rhubarb and turmeric to achieve a delicate balance point that maximizes weight loss while minimizes energy depletion. The relative weight percentage of astragalus may vary from between approximately 11% to approximately 15%. In one preferred embodiment of the present invention, the herbal composition contains 13.3% weight percent of astragalus.

Another ingredient, red sage root (*radix salviae miltiorrhizae*) enhances blood circulation and reduces serum levels of cholesterol and other lipids. Red sage has been described as containing tanshinone I, tanshinone IIA, tanshinone IB, isotanshinone I, isotanshinone II, miltirone, methyl tanshinonate, cryptotanshinone, isocryptotanshinone, dihydrotanshinone, tanshinol I, and tansinol II. Tanshinol I and tanshinol II are known to inhibit the proliferation of human tumorous cells (Ryu S Y, et al. Planta Medica, 1997, 63(4):339. Tanshinone exhibits myocardial protection and prevention of myocardial ischemia. It also prevents blood stagnancy in the lower abdomen, especially for those associated with menstrual pain. In a preferred embodiment, red sage root with the botanical name Slvia miltiorrhhiza Bge is used.

In the present invention, red sage root enhances the function of the cardiovascular system and counter-balances a common side effect of many weight loss drugs, increased risk of heart stress that can lead to actual tissue damage. The relative weight percentage of this ingredient may vary in a range of between approximately 11% to approximately 15%. In one preferred embodiment of the present invention, the composition contains 13.3% red saga root.

Dried ginger (*rhizoma zingiberis officinalis*) is usually produced by sun-drying the fresh rhizomes, and has been described as containing zingerone, zingiberene, zingiberol, gingerol, shogaol, phellandrene, and camphene. Zingerone, zingiberene, and zingiberol are known to alleviate vomiting and diarrhea, while zingiberene is an anti-inflammatory. In a preferred embodiment, a ginger species with the botanical name Zingiber officinale Rosc. is used. When used in an herbal decoction, the dried rhizomes are more potent than the fresh. Ginger aids digestion and assimilation, and is often added to herbal formulas to facilitate rapid delivery of the other herbs' therapeutic benefits. Ginger contains a digestive food enzyme called zingibain, which exceeds papain (derived from papaya) in digestive potency. Ginger also increases the concentration of the carbohydrate-digesting enzyme amylase in saliva. Further down the digestive tract, ginger improves digestion by activating peristalsis. Ginger can be used to relieve vomiting and to soothe the stomach and spleen.

In addition, research has found that ginger may help prevent strokes and the hardening of arteries. The active ingredient of ginger, gingerol, is believed to inhibit an enzyme that causes blood cells to clot. Ginger also lowers serum cholesterol, improves circulation, reduces platelet aggregation, and is a regulator of blood cholesterol. Ginger is also effective as a diaphoretic to encourage sweating to remove toxic waste and is used to increase kidney filtration.

As an ingredient of the present invention, dried ginger increases tolerance and reduces the side-effects of the remaining ingredients. Its relative weight percentage may vary in a range of between approximately 6% to approximately 8% of the composition. In one preferred embodiment of the invention, dried ginger constitutes 6–7% of the composition.

Herbal decoctions are produced by a characteristic method of preparing an aqueous extract of specific quantities of herbs. Traditionally, decoctions are prepared in a clay pot, but they can also be prepared in glass, unchipped enamel, or high-quality stainless steel containers without interfering with the herbs' properties. Decoctions should not be prepared in iron, copper, aluminum, or any other type of metal containers that can alter the chemistry of the herbs. The main advantages of an herb-derived composition prepared by the decoction method are thorough extraction of the herbs' complete medicinal potential, rapid absorption, and swift onset of therapeutic effects when administered.

Generally, a rhubarb-water mixture is prepared separately and added to a mixture of at least one of the remaining ingredients having been separately soaked to form an herbal mixture. When the herbal mixture contains each of turmeric, astragalus, red sage and ginger, the combination may be referred to as a four-herb mixture, and when combined with the rhubarb-water mixture, as a five-herb mixture. In one preferred embodiment, an herbal composition comprising rhubarb, astragalus, red sage root, turmeric, and dried ginger in accordance with the principles of the present invention is prepared by decoction as follows. A measured amount of the five herbs described above should be weighed according to the following proportions: 40.0% rhubarb roots, 26.7% turmeric roots, 13.3% astragalus roots, 13.3% red sage roots, and 6.7% dried ginger roots. The rhubarb roots are then placed in a first stainless steel container with a quantity of clean water approximately 6 to 8 times the weight of the rhubarb roots. Similarly, the other four herbs are placed together in a second stainless steel container with clean water approximately 6 to 8 times the combined weight of the herbs. When 1500 grams total weight of the herb mixture is used, the later for herbs are placed in 5400 ml water. All of the herbs are allowed to soak for 6 to 12 hours, preferably at least 8 hours. The herbal mixture is formed when the herbs and water in the second container are brought to a rolling boil, with constant stirring, and simmered at the boiling temperature for approximately 20 minutes (or until the fluid is reduced by half) to create a four-herb mixture. The cold rhubarb-water mixture in the first container is then added to the contents of the second container to yield a five-herb mixture. The combined mixture is heated to and maintained at about 85 to 95° C., or simmered at a temperature just below the boiling point of the mixture, for approximately 20 minutes with constant stirring. It is important not to heat the five-herb mixture to a boil because boiling removes very important rhubarb volatiles from the solution. The mixture is then allowed to cool to about 40 to 50° C. Neither ice nor any other cooling mechanism should be used for the cooling process, however, because the herbs must be allowed to react with each other during the slow cooling period. The resulting decoction exhibits the weight reducing effect of the invention although further processing may be performed to produce a composition in a particular form e.g. a concentrated liquid, powder, etc. or other formulation suited for a particular mode of administration.

To remove the insolubles, the cooled mixture is then filtered and strained by conventional methods, preferably at least twice by using multi-layered medium filter paper, filter press, centrifuge cloth-lined sieve or cheesecloth. The resulting warm final liquid extract may be directly administered orally, preferably between meals on an empty stomach for rapid assimilation.

In another embodiment, the above final liquid extract is then condensed into a concentrated liquid extract by evaporation. The concentrated liquid extract may be placed in a rotary evaporation flask and heated at the temperature below 85° C. until the extract is condensed to about $\frac{1}{10}$ of its original volume.

In another preferred embodiment, a conventional freeze-drying process is used to condense the final liquid extract into a powder form. Preferably, the final liquid extract is cooled at −80° C. and then placed on a standard laboratory freeze drier overnight to transform the extract into powder form. To create a lyophilizate, 10 mL of extract was quickly frozen in a dry ice/ethanol bath. The sample was freeze-dried for 13 hours, and a very fine powder was obtained. There was no evidence of gums or resins in this mixture. The 10 mL of extract yielded 0.5 g of particulate matter. The powder was dissolved in 0.68 mL of water and the resulting solution was slightly thick and dark brown in color, and yielded a product that is suitable for commercial use.

Both the final liquid extract and the freeze-dried powder contain a quantity of the herbal mixture with a dry weight in the range of 2 grams to 30 grams. The resulting herbal liquid or the powder may be incorporated into a pill, tablet or other pharmaceutically acceptable form and is then taken by patients as one dose with a daily dosage of up to three doses per day. Alternatively, the final liquid extract or powder form is mixed with a food or food supplement such as beverages, energy bars, protein or carbohydrate supplements or powders and other similar edibles. The total dosage administered will, of course, depend on the clinical indication of the patient or user. For the chronically or severely obese, higher dosages may be administered under the direct supervision of a physician who carefully monitors a patient's entire metabolic and biochemical profile. As a guideline, the total amount given to a patient daily should effect a targeted weight loss goal without causing side effects, such as excessive bowel movement or possible diarrhea. Generally, the maximum daily dosage is such that patients shall not have bowel movement three times more than usual after taking this supplement. In a clinical setting, the patient's physical reaction may be monitored after taking the first dose to decide whether the second or third dose should be given. The amount of the second or third dose may also be adjusted accordingly. In a preferred embodiment of this invention, the herbal mixture in powder form with dry weight of approximately 22.5 gram per day is given to patients. Alternatively, when the final liquid extract, the concentrated liquid, or the powder form is mixed in foods, the dosage can be altered to reflect the nature of the foods or the patterns of intended consumption ranging from the maximum permitted in the clinical setting described above to smaller dosages for over-the-counter foods or beverages.

Having generally described the present invention, a further understanding may be acquired by reference to the following examples, representing experimental studies conducted to investigate the effects of an herbal formula prepared as a decoction comprising rhubarb, astragalus, red sage root, turmeric, and dried ginger on weight reduction and body composition of rats.

EXAMPLES

Example 1

Male Sprague-Dawley Rats—2.5/5.0g Dry Berbal Administration

Male Sprague-Dawley rats were made obese by dietary intervention only. After 180 days, when their average weight reached about 620 grams, they were administered daily by stomach intubation (5 mL) either the amount of the decoction DRD extracted from 2.5 grams or 5.0 grams of the dry herbal. Over a 90-day treatment period, the rats administered the 2.5 grams DRD lost about 30% of their pre-treatment body weight, and the fat/lean ratio decreased by 13 fold. The rats administered the 5.0 grams DRD lost about 39% of their pre-treatment weight, and their fat/lean ratio decreased by 25 fold. The metabolic rates of the rats treated with either dose of DRD were restored to normal. The obese controls gained 20 grams and the normal rats gained approximately 103 grams over the 90-day treatment period. The weight loss of the rats receiving the DRD did not appear to have become asymptotic by the end of the 90-day experiment feeding period. Upon administering 5 grams of DRD in the period of 90 days, the blood sugar level of the obese rats was reduced by 40%. The level of triglyceride in the obese rats was reduced by 90%. The level of cholesterol was reduced by approximately 60%. The level of the LDL was reduced by 70%. While the level of HDL was increased by 70%. Treatment of the obese rats with the other lipid lowering drugs in parallel with DRD demonstrated that the lipid lowering effect of DRD was better than many other lipid lowering drugs, such as resins, statins, fibrates, and niacin.

Example 2

Male and Female Wistar Rats (Hypothalamic Lesions)—2.5/5.0g Dry Herbal Administration Male and female Wistar rats with hypothalamic lesions were made obese by providing the high caloric diet for 180 days, after which the male rats reached an average weight of about 580 grams and the female rats reached an average weight of about 430 grams. At that time, they received a daily administration of either 2.5 grams DRD or 5.0 grams DRD for 90 days by intubation (5 mL).

The male Wistar rats receiving the 2.5 grams DRD and 5.0 grams DRD lost about 36% and 41% of their pre-treatment body weight, respectively. The male obese control rats gained about 10 gram and the male normal control rats gained about 120 grams, (from a mean staring weight of approximately 423 grams), over the 90-day treatment period.

The females lost about 33% and 42% of their pre-treatment body weight when administered the 2.5 and 5.0 grams DRD, respectively. The loss of weight in both genders became asymptotic at about 45 days. The female obese controls maintained a constant weight and the female normal control rats gained about 50 grams (from a mean starting weight of approximately 350 grams) over 90-day treatment period.

Example #3

Male Wistar Rats—1.0/1.5/5:0 g Dry Herbal Administration

Young growing male Wistar rats, of about 220 grams average initial weight, were fed the obesity-inducing diet. Concomitantly, the rats were administered, 1.0 gram DRD, 1.5 grams DRD, or 5.0 grams DRD, by daily intubation, for 90 days. The treatment groups gained 21%, 24% and 47% less weight, respectively, than did the placebo controls. The rats administered fenfluramine gained 22% less weight than did the controls.

Administration of the herbal decoction of the present invention prevented weight gain in a high fat diet and a dose-dependent manner. The data and a morphological examination indicate that the rats that administered the decoction had significantly less parametrial fat than did the controls and slightly higher protein/fat ratios. Thus, the prevention of weight gain appears to be due to a reduction in fat storage, and that the skeletal muscle had been preserved. No significant adverse or side effects were observed in the rats administered the herbal decoction during the experimental period, nor was there any observed during the recovery period.

Example #4

Female Wistar Rats—Low/High Dose DRD (Aqueous Extract) 1.0/1.5/5.0 g Dry Herbal Administration Sixty female Wistar rats, averaging 220 g in weight, were randomly allotted to five experimental groups and fed the high fat diet described in Table I below for 56 days. The rats were housed individually in wire mesh cages equipped with an automated watering system. The room housing the rats was maintained at a temperature of 22° to 24° C., with a light-dark cycle of 12 hours each. Following the one-week quarantine period the rats were adapted to handling, and to oral insertion of the gastric intubation device over the next ten days. Water was intubated once a day during this period. After ten days, the rats no longer indicated marked distress during the procedure.

TABLE I

| Food Ingredient | Diet Composition |
| --- | --- |
| Casein | 287.0 |
| Starch | 238.0 |
| Corn oil | 32.0 |
| Crisco shortening[a] | 266.0 |
| Alphacel nonnutritive bulk[b] | 120.2 |
| Mineral mixture (AIN-76)[c] | 42.0 |
| Choline | 2.4 |
| dl-Methionine | 1.4 |
| Vitamin mixture (AIN-76)[d] | 11.0 |

[a]Proctor and Gambel, Cincinnati, OH
[b]ICN Biomedicals, Aurora, OH
[c]AIN mineral mix 76, ICM Biomedicals, Costa Mesa, CA
[d]AIN vitamin mix 76, ICM Biomedicals, Costa Mesa, CA After adaption to the intubation procedure, the diet of Table I was initiated. This diet is comprised of 56% of energy from fat. All treatment and placebo intubations occurred between 1600 and 1800 hours. Individual food intake was measured daily throughout the study. Body weight was measured daily through day 23 and twice weekly thereafter. The experimental period lasted 56 days. Lin, X., M. R. Chavex, R. C. Bruch, et al., *J. Nutrition* 128:1606–13, 1998.

Referring to Table II below, the five groups consisted of: the control group (n=15), which were fed ad libitum, and were intubated daily with 1 mL of water. The "low dose DRD" (n=10) and the "high dose DRD" (n=15) groups, which were fed ad libitum and administered daily 1 mL of the aqueous extract obtained from 0.75 grams and 1.50 grams of the initial dried herb mixture by intubation, respectively. The "fenfluramine group" (n=10), which was fed ad libitum and received 2 mg/kg fenfluramine in 1 mL of water daily, by intubation, and, finally, a fifth group (n=10) was pair-fed to the high dose DRD group and was administered 1 mL of water daily, by intubation.

TABLE II

| Group | n | Starting Weight, Gms | Treatment |
| --- | --- | --- | --- |
| C | 15 | 218.0 ± 16.8 | Control: vehicle (water) only by intubation; food and water ad libitum. |
| L | 10 | 214.3 ± 11.1 | Low dose DRD: 1 mL water extract from 0.75 g of the dry herbal mixture by intubation; food and water ad libitum |
| H | 15 | 226.0 ± 17.5 | High dose DRD: 1 mL water extract from 1.50 g of the dry herbal mixture by intubation; food and water ad libitum. |
| FF | 10 | 218.7 ± 18.9 | Fenfluramine: d-fenfluramine in vehicle (water) at 2 mg/kg of body weight; food and water ad libitum. |
| PF | 10 | 218.2 ± 12.3 | Pair fed: vehicle (water) only; food restricted to average of amount consumed by the H group the previous day; water ad libitum. |

Food consumption for all rats was determined daily, and body weights were obtained daily for the first 23 days, and then twice a week for the next 33 days. After 56 days all the rats except five from the control group and five from the high dose DRD group were sacrificed. Trunk blood was collected, and the eviscerated carcasses were homogenized, dried and assayed for body composition. White and brown fat depots, liver, kidney, spleen, heart, and gastrocnemius muscle were weighed. During the 56 days of the experiment, all rats were observed daily by the animal technician, and weekly by a veterinarian, and notations were made regarding physical activity/lethargy, fur condition, skin condition, eye condition, stools, and "others." There were no noticeable differences among any of the groups with regard to physical activity, skin condition, and eye condition. However, initially after intubation, the rats fed the DRD did exhibit some rubbing of the mouth and nose areas. This rubbing resulted in some alopecia. This behavior lasted about one week and then stopped. The other groups did not exhibit this rubbing.

The rats administered either dose of DRD had loose stools for the first few days. By the end of the first week the stools of the rats fed the low dose DRD were well formed and the consistency appeared normal. However, after one week the consistency of the stools of the rats fed the high dose DRD generally still appeared softer than the stools of the rats in the other groups. Soft stools were observed among the high dose DRD-treated rats from time to time during the course of the study. Additionally, the stools of both DRD groups were reddish in color, and remained so for the duration of the experiment.

The serum was analyzed for insulin, corticosterone and leptin, using standard commercially available immunoassays for the rat. Alkaline phosphatase, alanine aminotransferase, amylase, aspartate aminotransferase, chloride, cholesterol, creatinine phosphokinase, γ-glutamyl transpeptidase, glucose, hemoglobin, hematocrit, mean cell volume, platelets, potassium, sodium, triglycerides, and white blood cells were assayed by standard clinical laboratory methods. All data were pooled by treatment and subjected to a One-Way Analysis of Variance (ANOVA) followed by a Scheffe Comparison of Means analysis (for unbalanced groups). Statistix® for Windows, 1998. Analytical Software, Tallahassee, Fla. 32317.

The rats that were not sacrificed and had previously received the high dose DRD had their treatment withdrawn during a 14-day "recovery period." On the 15$^{th}$ day of this recovery period these rats, plus five control rats, were sacrificed and all the above analyses were conducted.

At time zero, the mean weights of the five groups were not different from each other. By the end of the first week the rats treated with fenfluramine had weight gain differences from the controls that would remain very consistent throughout the eight-week study (range from 14.0 to 19.6 grams). During the first half of the study, and especially during weeks two through four, the weight gain differences between the fenfluramine-treated rats and the controls paralleled those of the low dose DRD group. However, the fenfluramine weight gain differences remained constant for the remaining four weeks while the low dose DRD group substantially increased the weight gain difference from controls during this same period. The weight gain differences for the pair-fed rats mimicked those of the rats treated with high dose DRD. From the third to the eighth week the weight gain differences of the pair-fed rats ranged from 34.6 to 46.6 grams.

The data indicate that the high dose DRD treatment exerts an effect on the rats early in the treatment cycle, and that this effect remained fairly constant over the remaining course of the study. The low dose DRD rats exhibit a delay in reaching steady state in weight difference. The DRD may prevent or reduce the deposition of fat (especially in the parametrial region) in the female rat, and when a steady state is reached, this reduction remains constant throughout the study. This would account for the consistent difference in absolute weight, but not consistent differences in percent weight, seen in this study. The maximum effect of fenfluramine, although not as large as that ultimately seen with either DRD group, occurred by the end of the first week.

Figure 1:
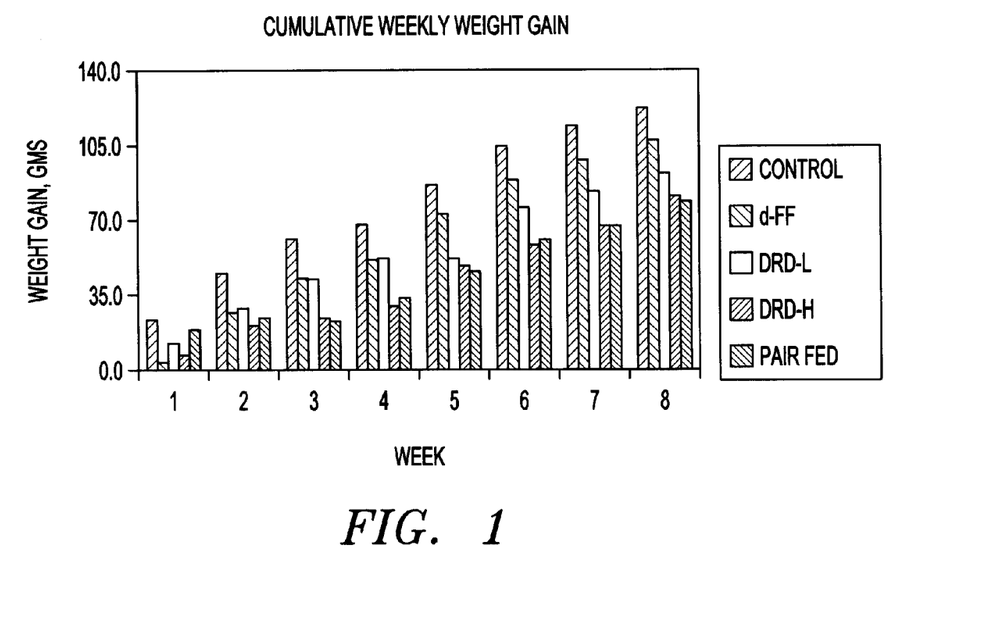
FIG. 1 shows the cumulative weekly weight gain (grams) measured over eight weeks in five groups of rats administered Fenfluremine (FF), a low dosage of one embodiment if the decoction of the invention (DRD-L), a higher dose of the decoction (DRD-H), a pair fed (PF) water-only group with a measured food intake, and a control.

Referring to FIG. 1, the cumulative weight gain for each animal was determined on days 7, 14, 21, 27, 34, 41, 48 and 56 (weeks 1 through 8). At days 7 and 14, average weight gains of the rats in each of the four treatment groups were significantly less than the weight gains of the controls, but not different from each other. Statistically significant separation among the remainder of the study. The control group gained the most weight. The weight gains for the group receiving low dose DRD and the group receiving fenfluramine were significantly less than that of the control group, but were not significantly different from each other. The weight gains for the group receiving the high dose DRD (Group 3), and the group being pair-fed to the high dose DRD group, were significantly less than the control group, the low dose DRD group, and the fenfluramine group, but not different from each other.

Figure 2:
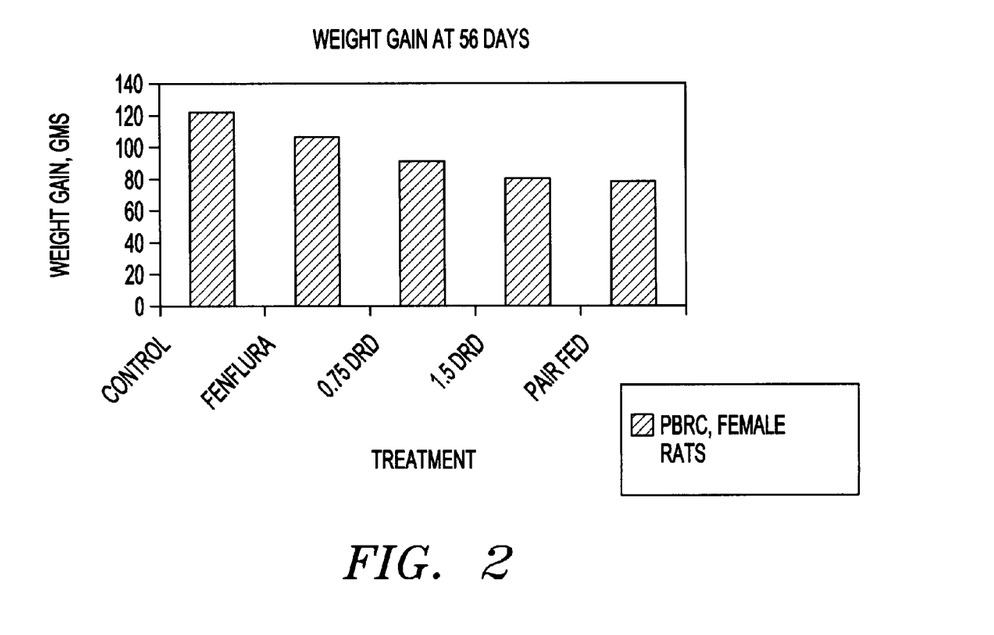
FIG. 2 shows weight gain (grams) at the 56 day interval for the five groups of FIG. 1.

On the $56^{th}$ day of treatment, the rats administered low dose DRD and high dose DRD had gained 24.6% and 33.4% less weight respectively than did the control rats. The rats administered fenfluramine gained 12.3% less weight than did the controls. Changes in body weight and weight gain over the eight week experimental period for the treatment groups are shown in TABLE III, and changes in weight gain are shown in FIG. 2.

TABLE III

| Treatment | Average Starting Weight, Gms ± SD. | Average Final Weight, Gms ± SD. | Average Gain, Gms ± SD |
|---|---|---|---|
| Control | 218.4 ± 16.8 | 340.3 ± 36.8 | 121.9 ± 25.3 |
| d-Fenfluramine | 218.7 ± 13.9 | 325.7 ± 33.7 | 106.9 ± 22.0 |
| Low dose DRD | 214.3 ± 11.1 | 306.2 ± 30.1 | 91.9 ± 29.0 |
| High dose DRD | 226.2 ± 17.7 | 307.4 ± 39.4 | 81.3 ± 26.5 |
| Pair Fed | 218.2 ± 12.3 | 296.9 ± 23.0 | 78.7 ± 18.7 |

The rats in the control group consumed significantly more total food than did the rats in any of the treatment groups over the 56-day period. The rats administered fenfluramine and low dose DRD consumed less total food over the 56 day period than the controls, but significantly more food than the rats fed the high dose DRD (and the rats that were pair-fed). The rats fed the high dose DRD and those that were pair fed ate significantly less total food over the 56 day period than did the other groups of rats, but the same as each other.

Figure 3:
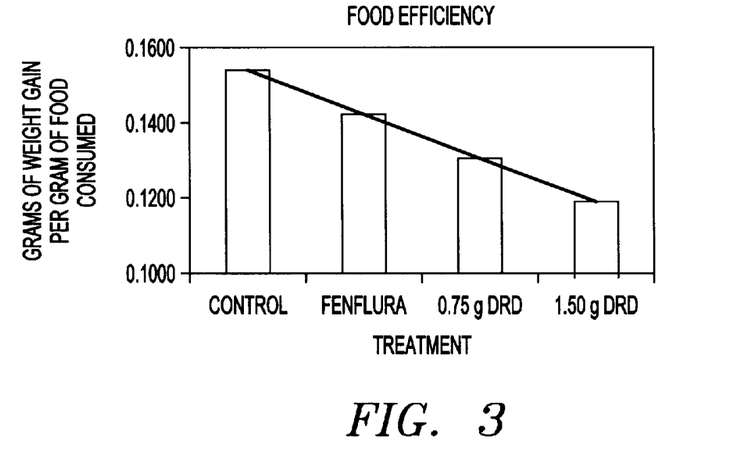
FIG. 3 shows food efficiency measured as grams of weight grain per gram of food consumed for the five groups of FIG. 1.

Weight loss due to decreased food efficiency suggests that a metabolic effect is occurring. At the end of the 56-day treatment period the control rats realized significantly greater food efficiency than did any of the treatment groups. Referring to FIG. 3, the food efficiencies of rats fed the low dose DRD and the rats fed fenfluramine, when calculated from grams of food ingested, were significantly greater than either the group in which rats were fed the high dose DRD or the group in which the rats were pair-fed. Rats fed the low dose and high dose DRD had food efficiencies that were 15.6% and 22.5% lower than controls, respectively. The food efficiency of the fenfluramine group was 7.8% lower than controls, suggesting a dose-related decrease in food efficiencies. Somewhat anomalously, the pair-fed group, which might be expected to have a higher food efficiency than fenfluramine or DRD-treated groups, had a lower food efficiency similar to that of the high dose DRD group. When food efficiency was calculated as a function of calories ingested, and requirements for basal metabolism were subtracted, differences in food efficiency existed between the groups. Pair-fed rats, fenfluramine rats, and low dose DRD rats exhibited somewhat lower food efficiencies than the controls, and the rats fed the high dose DRD had the lowest food efficiency. These differences between groups, however, did not reach statistical significance, but only reflected a trend (p=0.10).

Figure 4:
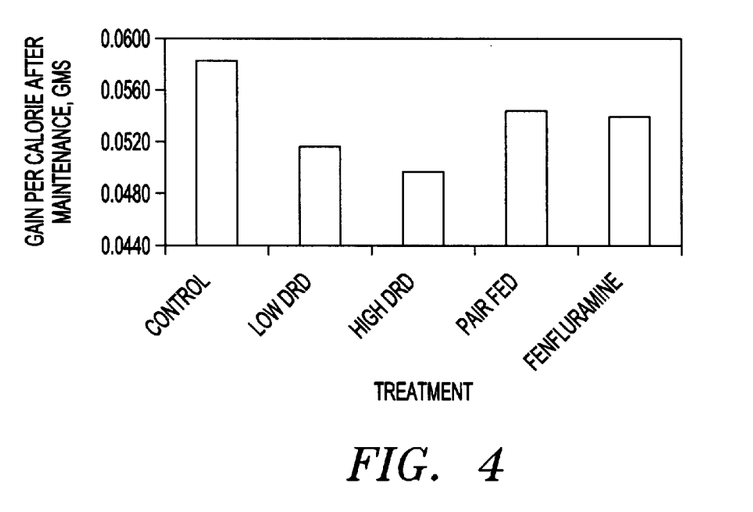
FIG. 4 shows food efficiency measured as weight gain per calorie of food ingested for the five groups of FIG. 1.

When food efficiency was calculated as a function of mean body weight and calories consumed, calories required for maintenance were subtracted from total calories consumed, yielding calories available for gain. Referring to FIG. 4, food efficiency may be expressed as the gain in weight for each calorie available for gain above maintenance. Thus, food efficiency for the control group, the fenfluramine-treated group, the pair fed group, and the groups administered low dose DRD, high dose DRD, was 0.0584, 0.0545, 0.0539, 0.0517, and 0.0497 grams respectively, per calorie remaining after the calories required for maintenance had been met.

The control group had the highest food efficiency; requiring only 17.09 ingested calories to cause a one-gram gain in weight. This value was obtained by dividing the actual gain per day (2.18 grams) by the daily energy available for gain (37.20 calories). The groups administered low dose DRD and fenfluramine required 18.83 and 18.16 calories to cause a one-gram weight gain respectively, and thus had lower food efficiencies than the control. The group administered the high dose DRD, however, had the lowest food efficiency, requiring 19.35 calories to gain the same one-gram. The pair-fed rats required less calories than did the high dose DRD-treated group to gain the same weight. The amount of calories required by the pair-fed rats, 18.14, is similar to that required by the low dose DRD-treated and fenfluramine-treated rats.

No differences were found between the groups for any of the serum indices evaluated after the 56-day experimental period, with the exception of leptin. There is generally a direct positive correlation between the quantity of leptin in the blood and the amount of body fat and an increase in the risk of diabetes mellitus. At the end of the 56-day treatment period, the control rats had significantly more leptin in their blood than did the other treatment groups. The rats administered fenfluramine had less leptin than controls, but significantly more than the rats administered either dose of DRD or the pair-fed rats. The differences in leptin values continued during the 14-day recovery period despite the withdrawal of DRD, but this might be expected due to the modest weight gain seen during that period.

Serum insulin levels reflect the metabolic processes related to carbohydrate and fat storage and usage for energy. Corticosterone is a hormone necessary to combat stress and maintain intermediary metabolism. There were no statistical differences between the serum insulin or corticosterone levels for the controls or any of the treatment groups suggesting that the treatments did not adversely affect the rats' metabolism, nor did they cause stress.

The data demonstrate that the herbal decoction of the invention significantly reduces weight gain in growing female rats fed a high fat diet when compared to controls.

Figure 5:
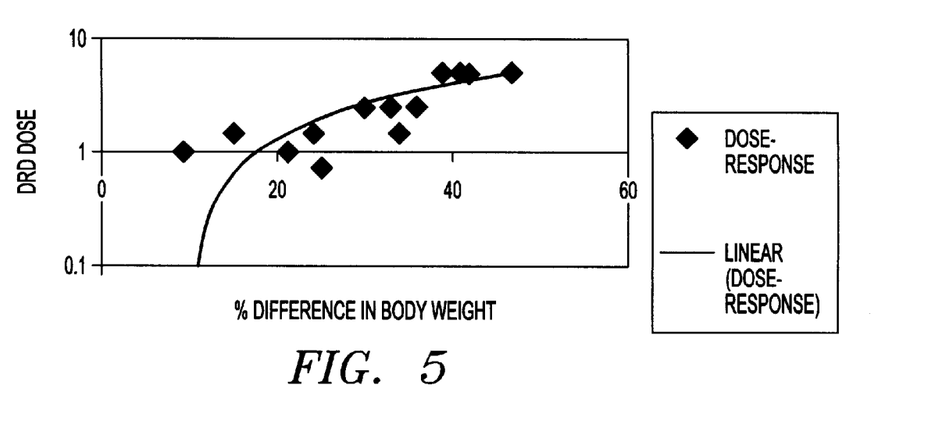
FIG. 5 shows a dose response curve measuring the percent difference in body weight as a function of five different dosages of the decoction.

The rats administered the high dose DRD and low dose DRD gained 33.4% and 24.6% less weight, respectively, than did the controls. Further, this weight reduction appears to occur in a dose-dependent manner, as shown in FIG. 5. The regression analysis of the computer-generated dose-response curve yields a relationship with a $r^2$ value of 0.73 and an r value of 0.85, with a significance of greater than 99%. Increasing the dosage did increase the weight difference effect. However, it appears that a dose of approximately 2.5 g of original plant material equivalent/mL is an effective and efficient dose that results in substantial differences in weight between treated and control rats.

Figure 6A:
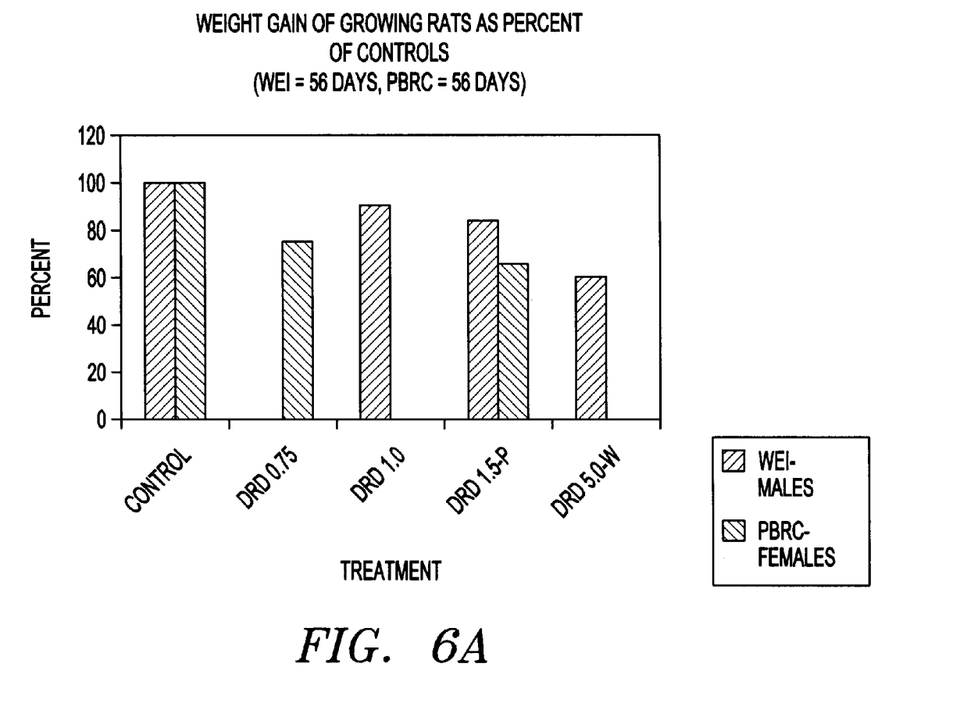
FIG. 6A shows weight gain in rats fed either an obesity-inducing diet alone, or the diet plus the DRD decoction at day 56.

Referring to FIG. 6A, the weight gain data for the DRD-treated male rats as a percent of control for the animals in Example 3 at 56 days was compared to the weight gain data for the DRD-treated female rats in Example 4 as a percent of control at 56 days. At 56 days the percent weight gain trends of the DRD-treated rats in both studies were similar, but the female rats in Example 4 showed greater differences from controls (gained less weight as a percent of the controls) than did the male rats in Example 3.

Figure 6B:
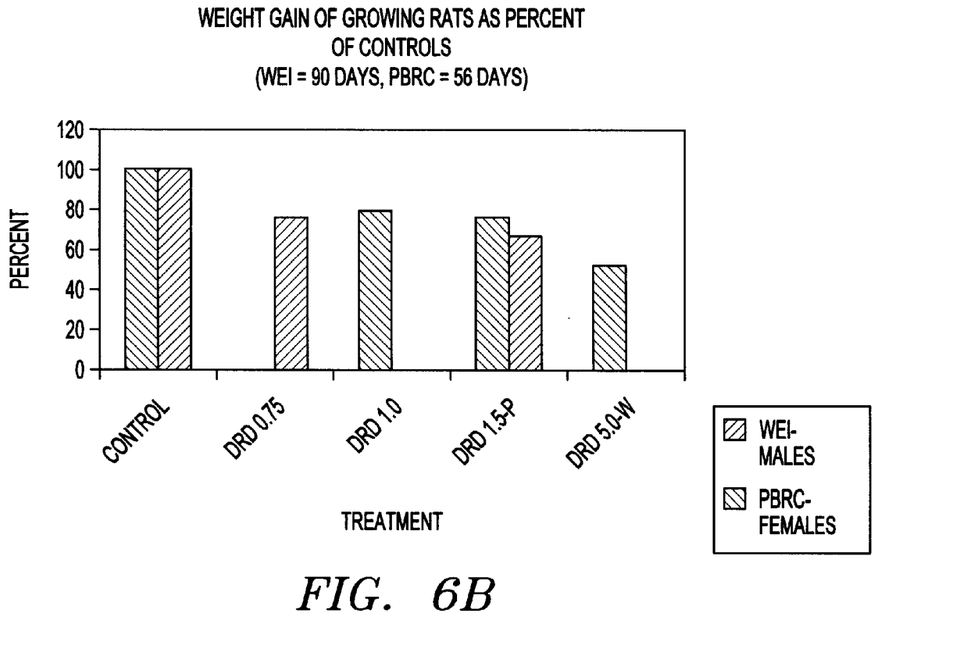
FIG. 6B shows the same study at day 90.

However, referring to FIG. 6B, when the weight gains as a percent of control weights in Example 4 were compared to later time periods of the study in Example 3, the differences from controls were similar. In Example 3, at 65 days the percent differences between the DRD-treated male rats and the controls reached the level at which they would generally remain for the duration of the 90-day study.

Figure 7:
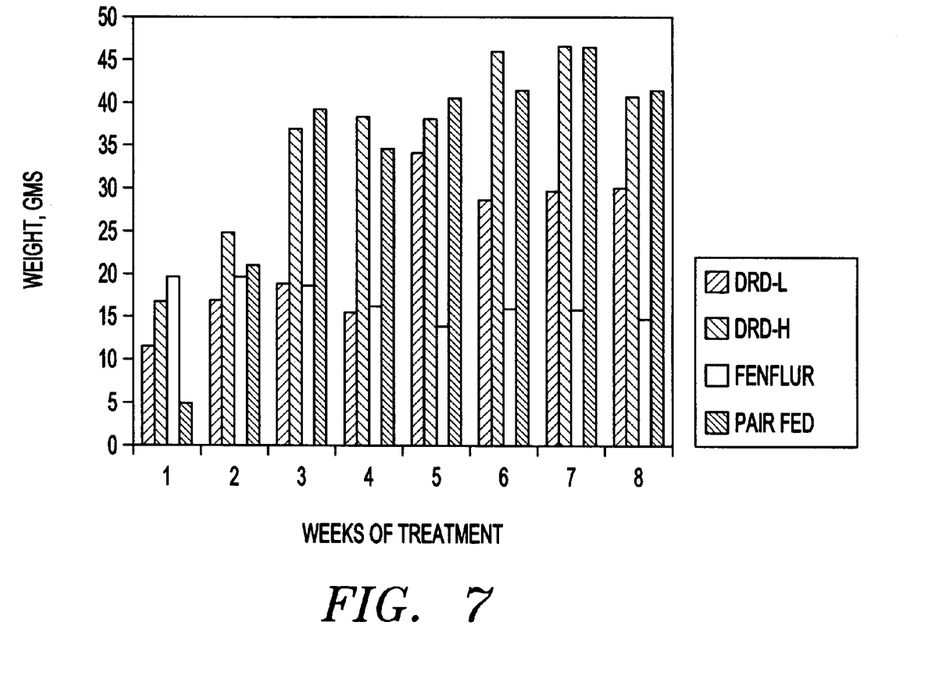
FIG. 7 shows the differences in absolute weight of the animals in the five groups of FIG. 1 measured over 56 days.

Referring to FIG. 7, the weight of all treated groups in Example 4 were compared to the weight of controls for weeks one through eight and the differences in absolute weight between the groups were evaluated. The data indicate that the differences in weight between the rats treated with high dose DRD and the controls increased for the first three weeks, and these differences then generally remained consistent (range of 36.9 to 46.5 grams) until the end of the study. The rats treated with low dose DRD maintained a fairly consistent difference in weight from the controls for the first four weeks (range of 11.4 to 18.8 grams). During the fifth week, however, the difference increased, and this increase remained consistent for the remaining four weeks of the study (range of 28.6 to 34.0).

Figure 8:
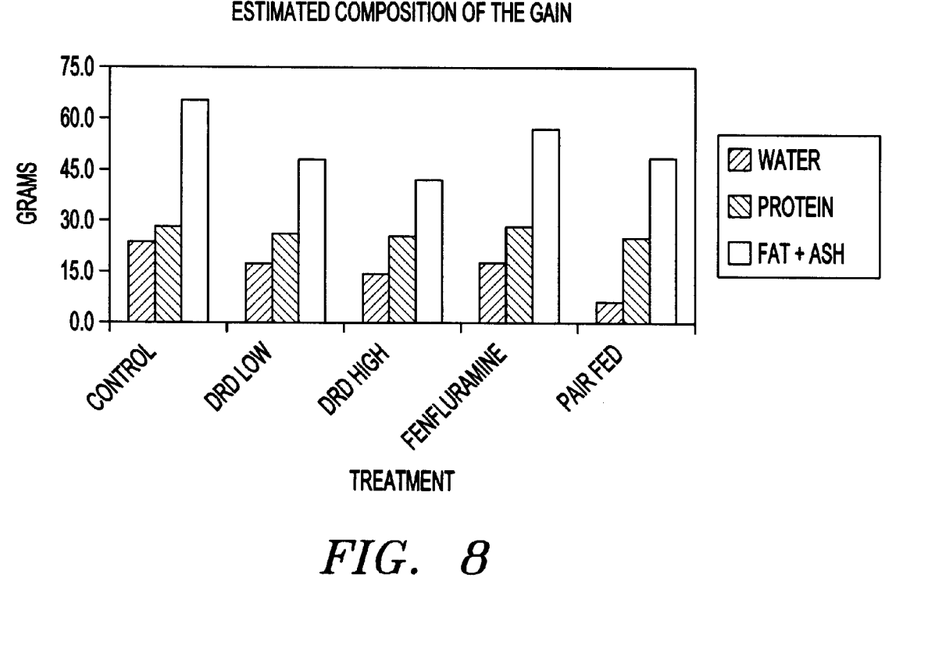
FIG. 8 shows the difference in weight gain of each body composition component over day 56 for the five groups of FIG. 1.

Although the percent total body fat of the rats determined at the end of the study was not significantly different among any of the groups, the amount of parametrial fat in the rats administered high dose DRD was significantly less than any other group of rats. The rats administered low dose DRD and the pair-fed rats had more parametrial fat than did the high dose DRD rats, but significantly less than either the controls or the rats administered fenfluramine. Referring to FIG. 8, when body compositions, and respective grams of fat+ash, protein, water, and fat, of 220 gram rats were compared to like indices of the rats after 56 days of treatment, the control rats had gained significantly more weight as fat than did any of the other rats. The rats administered the low dose DRD and the fenfluramine gained significantly less fat than did the controls, and the rats fed the high dose DRD gained the least amount of fat and the differences were significantly different from all other groups. The gain in protein, however, was not different among any of the groups, indicating that the differences in lack of weight gain could be attributed to lack of fat gain but not lack of protein gain.

In conclusion, administration of the DRD herbal decoction significantly prevented weight gain in rats fed the high fat diets, in a dose-dependent manner. Also, the rats administered the DRD decoction had significantly less parametrial fat than did the controls. Both DRD groups also had higher protein/fat ratios than the pair fed rats and the controls, although not significantly so, indicating that the prevention of weight gain was due to a reduction in fat storage, and that the skeletal muscle had been preserved.

The reduction in weight gain experienced by the groups administered DRD also involved a reduction in food ingestion caused by a probable anorectic effect. Rats fed the low dose and high dose DRD had food efficiencies that, when measured as a function of grams of food ingested, were significantly 15.6% and 22.5% lower than controls, respectively, but were not lower than the pair-fed rats. When measured as a function of energy ingested statistical significance was not reached, but a trend (p=0.10) was observed. The control rats had the highest food efficiency (exhibited the greatest gain per calorie remaining after maintenance requirements were met). The pair-fed rats and the rats administered fenfluramine and low dose DRD were grouped together with lower food efficiencies than the controls, and the rats fed the high dose DRD had the lowest food efficiency.

There will be various modifications, improvements, and applications of the disclosed invention that will be apparent to those of skill in the art, and the present application encompasses such embodiments to the extent allowed by law. Although the present invention has been described in the context of certain preferred embodiments, the full scope of the invention is not so limited, but is in accord with the scope of the following claims.

I claim:

1. An herbal composition for hindering weight gain comprising: rhubarb, turmeric, astragalus root, red sage root, and ginger root.

2. The herbal composition of claim 1 wherein the weight percentage of rhubarb is between approximately 36 to 44%.

3. The herbal composition of claim 1 wherein the weight percentage of turmeric is between approximately 24 to 30%.

4. The herbal composition of claim 1 wherein the weight percentage of astragalus is between approximately 11 to 15%.

5. The herbal composition of claim 1 wherein the weight percentage of red sage is between approximately 11 to 15%.

6. The herbal composition of claim 1 wherein the weight percentage of dried ginger root is between approximately 6 to 8%.

* * * * *